US008071759B2

(12) United States Patent
Huang et al.

(10) Patent No.: US 8,071,759 B2
(45) Date of Patent: Dec. 6, 2011

(54) WATER SOLUBLE CHOLESTEROL DERIVATIVES

(75) Inventors: Lijun Huang, Waterville, OH (US); Benjamin R. Travis, Maumee, OH (US)

(73) Assignee: Affymetrix, Inc., Santa Clara, CA (US)

( * ) Notice: Subject to any disclaimer, the term of this patent is extended or adjusted under 35 U.S.C. 154(b) by 214 days.

(21) Appl. No.: 12/494,159

(22) Filed: Jun. 29, 2009

(65) Prior Publication Data
US 2010/0016563 A1    Jan. 21, 2010

Related U.S. Application Data

(60) Provisional application No. 61/082,114, filed on Jul. 18, 2008.

(51) Int. Cl.
C07H 1/00    (2006.01)
(52) U.S. Cl. .................... 536/123.1; 536/123
(58) Field of Classification Search .................. None
See application file for complete search history.

(56) References Cited

U.S. PATENT DOCUMENTS

| | | | |
|---|---|---|---|
| 4,194,067 A | 3/1980 | Keyes | |
| 4,247,647 A | 1/1981 | Barabino et al. | |
| 5,674,987 A | 10/1997 | Gray | |
| 5,763,586 A | 6/1998 | Gray | |

FOREIGN PATENT DOCUMENTS
EP    1014947    7/1998

OTHER PUBLICATIONS

Pohlentz et al. Glycoconjugate Journal (1996), vol. 13, pp. 147-152.*
Beel et al., "Direct binding of cholesterol to the amyloid precursor protein: An important interaction in lipid-Alzheimer's disease relationships?", Biochimica et Biophysica Acta, 1801(8): 975-982 (Aug. 2010).
Beel et al., "Structural Studies of the Transmembrane C-Terminal Domain of the Amyloid Precursor Protein (APP): Does APP Function as a Cholesterol Sensor?", Biochemistry, 47(36):9428-9446 (Aug. 2008).
Howell et al., "CHOBIMALT: A Cholesterol-Based Detergent," Biochemistry, online publication (Oct. 2010).
Anatrace SBIR Grant No. R43GM069021, Melvin H. Keyes, Detergents for Dissociation of Lipid Rafts., Published Sep. 2003.
Anatrace SBIR Grant No. R43MH081379, Benjamin Travis, Novel Membrane-Mimetic Media for Brain Derived GPCRs., Published Sep. 5, 2007.
Beel, A.J., et al., Biochemistry 2008, vol. 47, pp. 9248-9446.
Biessen, E.A., et al; Arterioseler Thromb. Vasc. Biol., 16, 1552-8 (1996).
Biessen, E.A.L., et al; J. Med. Chem., 38, 1846-1852 (1995).
Brito, R.M.M. and Vaz, W.L.C., Anal. Biochem., 152, 250-255 (1986).
Brown, D.A. and London, E., Annu. Rev. Dev. Biol., 14, 111-36 (1998).
Brown, D.A. and London, E., Biochem. Biophysics. Res. Commun., 240, 1-7 (1997).
Brown, D.A. and Rose, J.K., Cell, 68, 533-544 (1992).
Brown, R.E., J. of Cell Science, 111, 1-9 (1998).
Caffrey, et al; J. Mol. Biol., 271, 819-826 (1997).
Clore, G.M. and Gronebom, A.M., Treds in Biotechnology, 16, 22-34 (1998).
Dzizenko, A.K., et al; PMR spectra of acetylated steroid and triterpenoid glycosides, Carbohydrate Research (1973), 27(1), 249-53.
Ershov, P.V., et al; Biosensor analysis of the interaction of potential dimerization inhibitors with HIV-1 protease; ISSN 1990-7508, Biochemistry (Moscow) Supplement Series B: Biomedical Chemistry, 2009, vol. 3, No. 3, pp. 272-288.
Garavito, R.M. And Ferguson-Miller, S., J. Biol. Chem., 276, 32403-32406 (2001).
Garavito, R.M. and Picot, D., Methods: A companion to methods in enzymology, 1, 57-69 (1990).
Gilliland, G.L. and Davis, D.R. Meth. Enzymol., 104, 370-381 (1984).
Gorzelle, B.M., et al; Biochemistry, 38, 16373-16382 (1999).
Gorzelle, B.M., et al; J. Am. Chem. Soc., 124, 11594-11595 (2002).
Hashimoto, K., et al; J. Polym. Sci., Part A: Poly. Chem., 29, 1271 (1991).
Hekman, M., et al., EMBO Journal, 3, 3339-3345 (1984).
Hjelmeland, L.M., et al; Anal. Biochem., 130, 485-490 (1983).
Hjelmeland, L.M., The design and synthesis of detergents for membrane biochemistry in methods in enzymology, 124, 135-164 (1986).
Isabell, H.S. and Schaffer, R., Rethods Carbohydr. Chem., 2, 16-18 (1983).
Isakov, V.V., et al; A study of acetylated glycosides and maltosides of some steroids by the 1H-NMR method; Institute of Biologically Active Substances, Far-Eastern Scientific Center, Academy of Sciences of the USSR. Translated from Khimiya Prirodnykh Soedinenii, No. 1, pp. 78-81, Jan.-Feb. 1972. Original Article submitted Oct. 15, 1971.
Kay, L.E. and Gardner K.H., Curr Opin. Struct Biol., 1, 752-731 (1997).
Kempen, H.J.M., et al; J. Med. Chem., 27, 1306-1312 (1984).
Keyes, et al; Solubilizing detergents for membrane proteins, in methods and results in membrane protein crystallization; International University Line, LaJolla, CA So Iwata, Ed. (2002).
Klein, B., et al; Clin. Chem., 20, 482-485 (1974).
Kuehlbrandt, W., Quart Rev. Biophys., 21, 429-477 (1988).
Luria, A. et al., Biochemistry, 41, 13189-13197 (2002). Mirzabebov, et al., Journal of Biological Chemistry, 274, 28745-28750 (1999).
Moffett, S., et al, J. Biol. Chem., 275, 2191-2198 (2000).
Nagy, J.K., Hoffmann, et al; Use of amphipathic polymers to deliver a membrane protein to lipid bilayers; FEBS letters, 501, 115-120 (2001).
Reichstein, T., and Reich, H., The chemistry of the steroids; Annu. Rev. Biochem. 1946. 15:155-192.
Roelen, H.C., et al; J. Med. Chem., 34, 1036-42 (1991).
Rosen, M.S., Surfactants and interfacial phenomenon, p. 224, Wiley, New York, (1978).

(Continued)

Primary Examiner — Patrick Lewis
(74) Attorney, Agent, or Firm — Thomas J. Siepmann

(57) ABSTRACT

Four novel water soluble cholesterol derivative compounds are disclosed. These compounds have various applications in studies of membrane proteins, including drug screening and studies of receptor stability and folding. In one aspect the water soluble cholesterol derivatives disclosed may be used to replace cholesterol in micelle-solubilized membrane protein preparations.

11 Claims, 2 Drawing Sheets

OTHER PUBLICATIONS

Samsonoff, C., et al; J. Colloid Interface Sci., 109, 325-329 (1986).
Segal, R., et al; Hemolytic properties of synthetic glycosides, Journal of Pharmaceutical Sciences (1978), 67(11), 1589-92.
Simons, K. and Ikonen, E., Nature, 387, 569-72 (1997).
Simons, K. and Toomre, D., Nature Revs. Molec. Cell Biol., vol. I, 31-41 (2000).
Stadel, et al; Trends pharmacol. Sci.m 18, 430-437 (1997).
Thuresson, E.D., et al; J. Biol. Chem., 276, 10347-59 (2001).
Thruesson, E.D., et al; J. Biol. Chem., 276, 10358-65 (2000).
Uvarova et al., "Synthesis of glycosides of some steroids,"Chem. Nat. Compounds, 7(6):824-825, 1971.
Vendittis, E.D., et al; Anal. Biochem., 115, 278-286 (1981).
Watson, J. D. and Crick, F.H., Nature, vol. 171, 737-738 (1953).
Wu, W.G. and Chi, L.M., J. Am. Chem. Soc., vol. 113, 4683-4685 (1991).

* cited by examiner

FIGURE 1 A, B
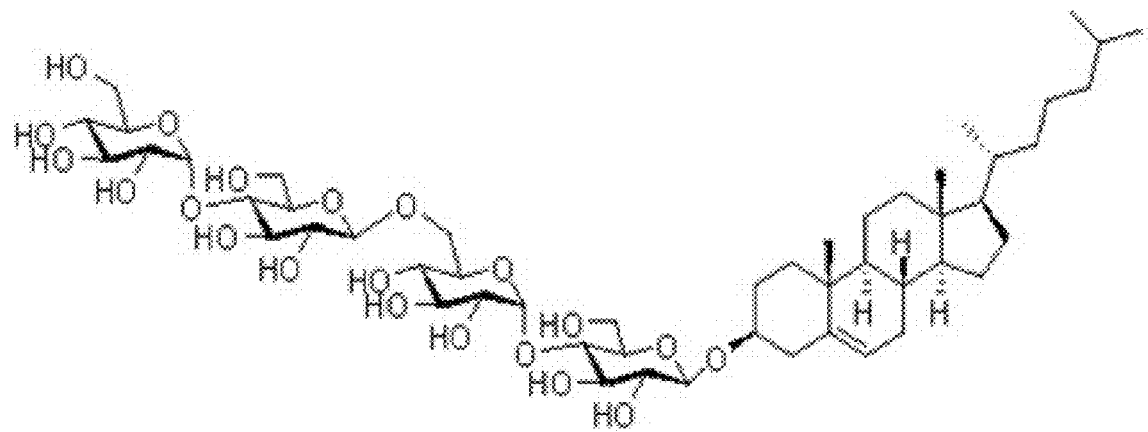
A
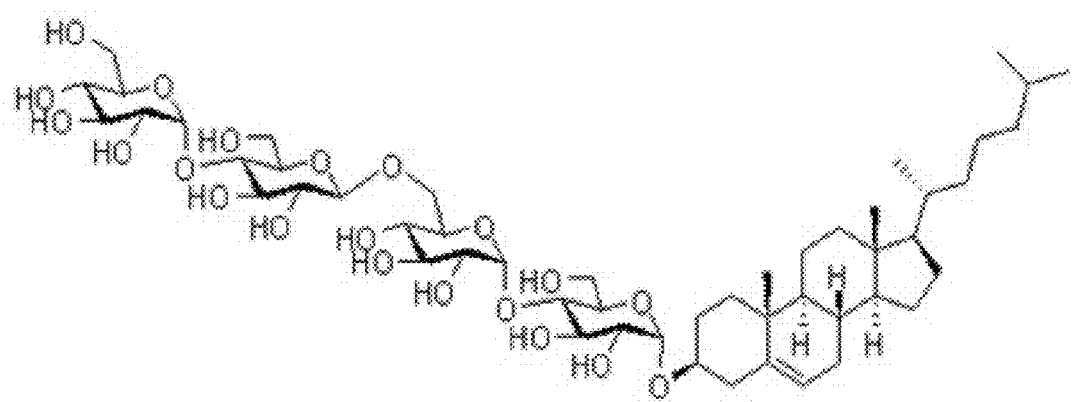
B

FIGURE 1 C, D
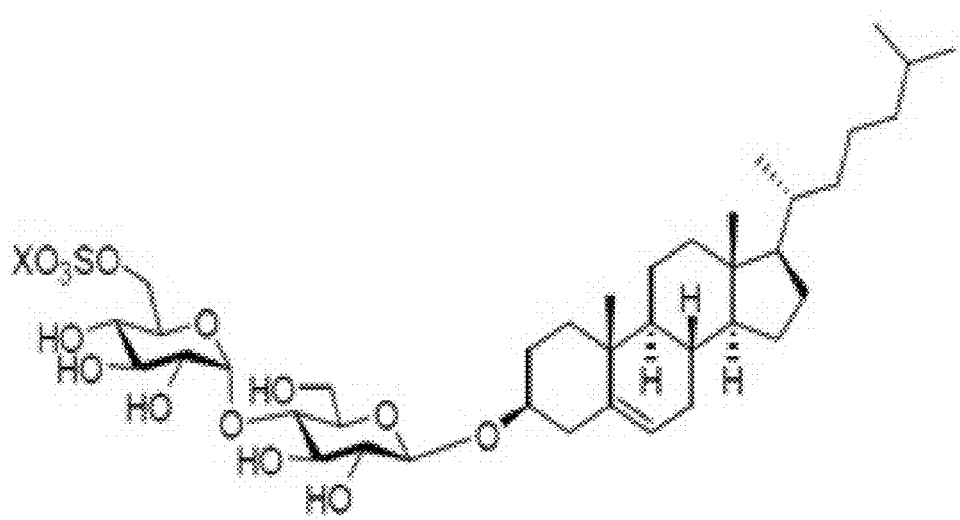
C
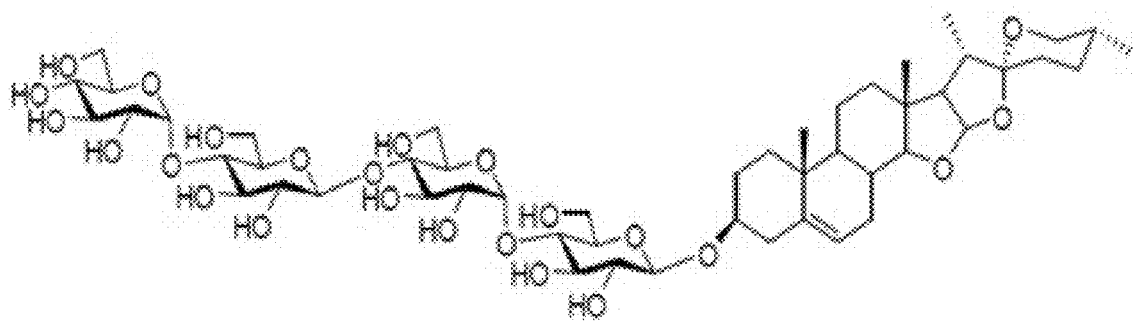
D

WATER SOLUBLE CHOLESTEROL DERIVATIVES

REFERENCES TO RELATED APPLICATIONS

The present application claims priority to U.S. Provisional Patent Application Ser. No. 61/082,114, filed on Jul. 18, 2008, which is hereby incorporated herein by reference in its entirety for all purposes.

STATEMENT OF FEDERALLY SPONSORED RESEARCH

This invention was made with government support under Small Business Innovation Research (SBIR) Program grant number R43MH081379 awarded by the National Institutes of Health. The government has certain rights in the invention.

FIELD OF THE INVENTION

The present invention relates generally to water-soluble derivatives of cholesterol and methods for their synthesis and use.

BACKGROUND OF THE INVENTION

In order to be fully functional, many cellular receptors and other membrane proteins require interactions with cholesterol within the lipid bilayer. Therefore, when reconstituting these proteins for in vitro biochemical and structural studies, it is desirable to mimic the native bilayer as closely as possible. This can be accomplished by adding the appropriate lipids and cholesterol to micelle-solubilized membrane protein preparations. One obstacle however, is that cholesterol is notoriously difficult to solubilize under the micellar conditions typically used for membrane protein solubilization. In the present invention, four novel water soluble cholesterol analogs are disclosed which have various applications in studies of membrane proteins.

SUMMARY OF THE INVENTION

We have prepared four water-soluble cholesterol derivatives depicted in the Figures. FIG. 1A is Cholesterol-β-tetrasaccharide (1), FIG. 1B is Cholesterol-α-tetrasaccharide (2), and FIG. 1C is Cholesterol-β-sulfated maltoside (3). FIG. 1D is Diosgenin-β-tetrasaccharide (4). In one embodiment, the compounds are made by multi-step chemical synthesis from commercial cholesterol or diosgenin (other steroids are potential substrates and are denoted as 'cholesterol derivative') and maltose.

In preferred aspects, the tetrasaccharide is prepared via selective coupling of two differentiated units of a protected maltose. For each compound a final coupling step between the cholesterol derivative and the saccharide is required. Descriptions of alpha and beta are descriptors of the anomeric linkage between the cholesterol derivative and the first sugar. Each compound can be made on a scale of up to 5 g and they are soluble up to 5% w/v in water.

BRIEF DESCRIPTION OF THE DRAWING

The accompanying drawing, which is incorporated in and forms a part of this specification, illustrates embodiments of the invention and, together with the description, serves to explain the invention:

FIG. 1A shows the structure of Cholesterol-β-tetrasaccharide (1). FIG. 1B shows the structure of Cholesterol-α-tetrasaccharide (2). FIG. 1C shows the structure of Cholesterol-β-sulfated maltoside (3). FIG. 1D shows the structure of Diosgenin-β-tetrasaccharide (4).

DETAILED DESCRIPTION OF THE INVENTION

General

The present invention has many embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

Definitions

Cholesterol is a lipid compound with a molecular formula $C_{27}H_{46}O$, consisting of three structurally distinct regions: i) a rigid sterol ring, ii) a flexible alkyl chain, together forming the hydrophobic portion of the molecule, and iii) 3β-hydroxyl moiety, which is the only polar group in cholesterol and gives the molecule its amphiphatic character. Cholesterol is an essential component of cell membranes in all eukaryotes, with crucial roles in membrane organization, dynamics, function and sorting.

Cholesterol is found distributed non-randomly in domains and pools in biological membranes, and has been reported to modulate conformation (and hence function) of integral membrane proteins, either through a specific molecular interactions, or through alterations in the membrane physical properties induced by the presence of cholesterol.

An example of a membrane protein family regulated by cholesterol is the seven transmembrane domain G-protein coupled receptors (GPCRs). The GPCR family has over 800 members, representing approximately 2% of total proteins encoded by the human genome. GPCRs have diverse signaling functions, mediating responses to both endogenous and exogenous ligands via recruitment and activation of heterotrimeric G-proteins to the cytoplasmic side of the cell membrane. GPCR-activated heterotrimeric G-proteins in turn regulate a multitude of physiological processes ranging from neurotransmission and cellular differentiation and growth to inflammatory and olfactory responses. Therefore, GPCRs represent major targets for the development of new drugs.

The term liposome, as used in this application, refers to a vesicular structure composed of a lipid bilayer separating an aqueous internal compartment from the bulk aqueous phase. Liposomes can be composed of naturally-derived phospholipids with mixed lipid chains, or of pure surfactant components such as DOPE (dioleoylphosphatidylethanolamine).

The term micelle, as used in this application, refers to closed lipid monolayers with a fatty acid core and polar surface, or for an inverted micelle, a polar core with fatty acids on the surface. Due to their unique structure, both liposomes and micelles have been used in vitro studies of protein function as well as drug delivery.

The term water-soluble cholesterol derivative, as used in this application, refers to cholesterol analogs containing a water-soluble head group or moiety.

Water-Soluble Cholesterol Derivatives

Commercially available water-soluble cholesterol derivatives, such as cholesterol hemisuccinate and cholesterol sulfate, have been used as cholesterol substitutes in studies of membrane protein function and structure. These cholesterol analogs contain anionic head groups, making them more suitable for micellar membrane protein preparations. However, cholesterol hemisuccinate and cholesterol sulfate remain difficult to solubilize in detergent micelles, and their anionic head groups make them not biochemically optimal for in vitro protein studies. Therefore, there remains a need for the development of water-soluble cholesterol derivatives that can be better utilized in biochemical and structural studies of membrane proteins.

To address this issue, we have synthesized novel, water-soluble cholesterol derivatives that can be used to enhance the solubility and functionality of micelle-solubilized membrane proteins for biochemical and structural studies. These compounds will likely be useful in other applications that benefit from abundant quantities of pure and properly-folded membrane proteins (ie, GPCRs), including drug screening and studies of receptor stability and folding.

In a preferred aspect, the compounds are made by multi-step chemical synthesis from commercial cholesterol or diosgenin (other steroids are potential substrates and are denoted as 'cholesterol derivative') and maltose.

In preferred aspects, the tetrasaccharide is prepared via selective coupling of two differentiated units of a protected maltose. For each compound a final coupling step between the cholesterol derivative and the saccharide is required. Descriptions of alpha and beta are descriptors of the anomeric linkage between the cholesterol derivative and the first sugar.

Each compound can be made on a scale of up to 5 g and they are soluble up to 5% w/v in water.

CONCLUSION

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes.

What is claimed is:

1. Cholesterol-β-tetrasaccharide according to Formula I:

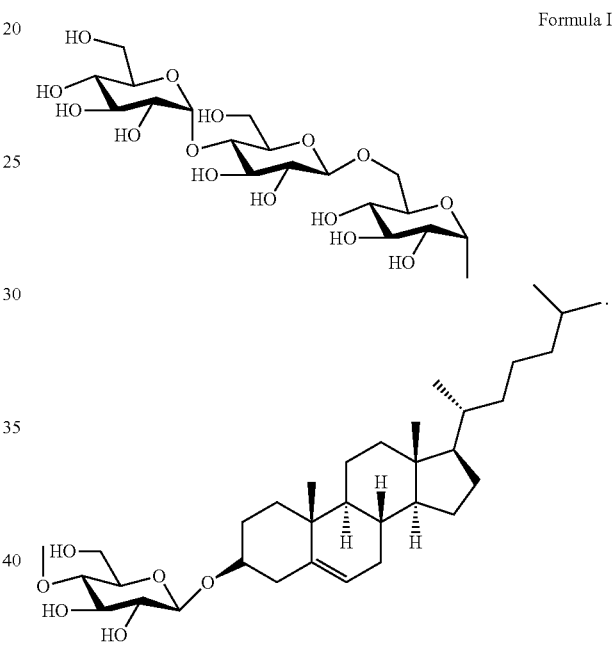

Formula I

2. Cholesterol-α-tetrasaccharide according to Formula II:

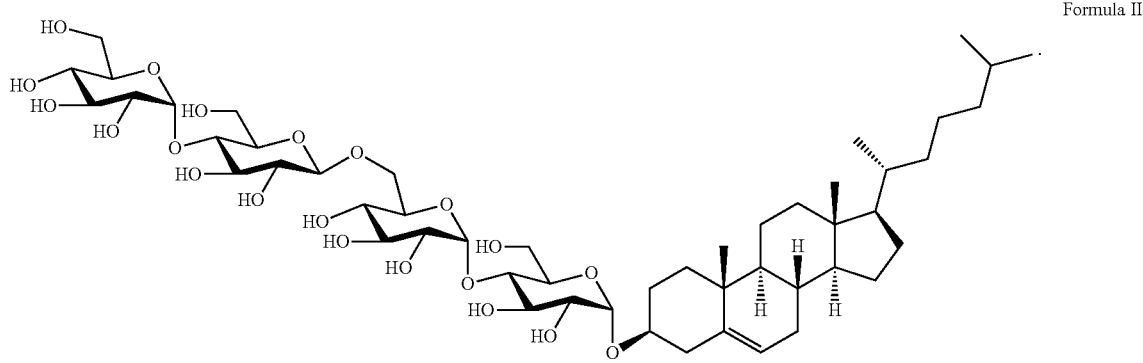

Formula II

3. Cholesterol-β-sulfated maltoside according to Formula III, wherein X is selected from the group consisting of Me$_3$NH, NH$_4$, and Na:

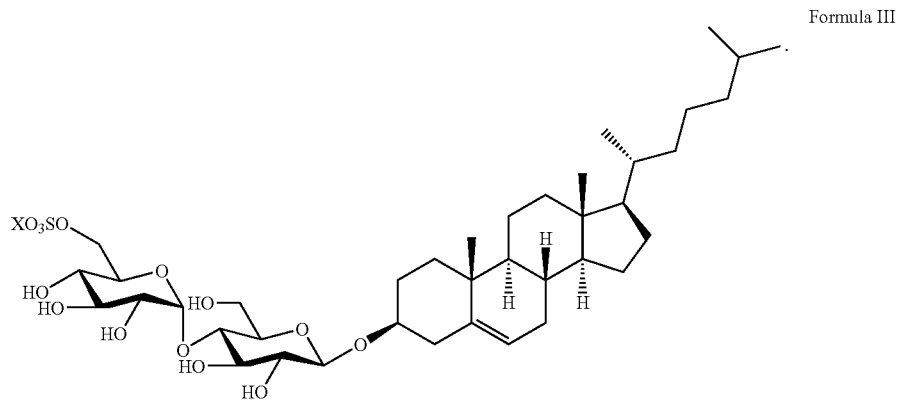

Formula III

4. Diosgenin-β-tetrasaccharide according to Formula IV:

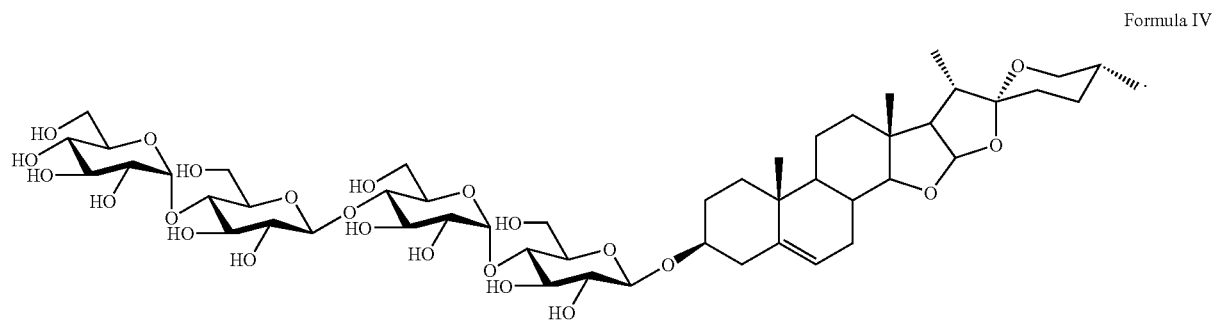

Formula IV

5. A composition comprising the cholesterol-β-tetrasaccharide according to claim 1.

6. A composition comprising the cholesterol-α-tetrasaccharide according to claim 2.

7. A composition comprising the cholesterol-β-sulfated maltoside according to claim 3.

8. A composition comprising the diosgenin-β-tetrasaccharide according to claim 4.

9. A method of reconstituting membrane proteins in a lipid bilayer, comprising:
   providing membrane protein;
   providing at least one cholesterol derivative selected from the group consisting of:

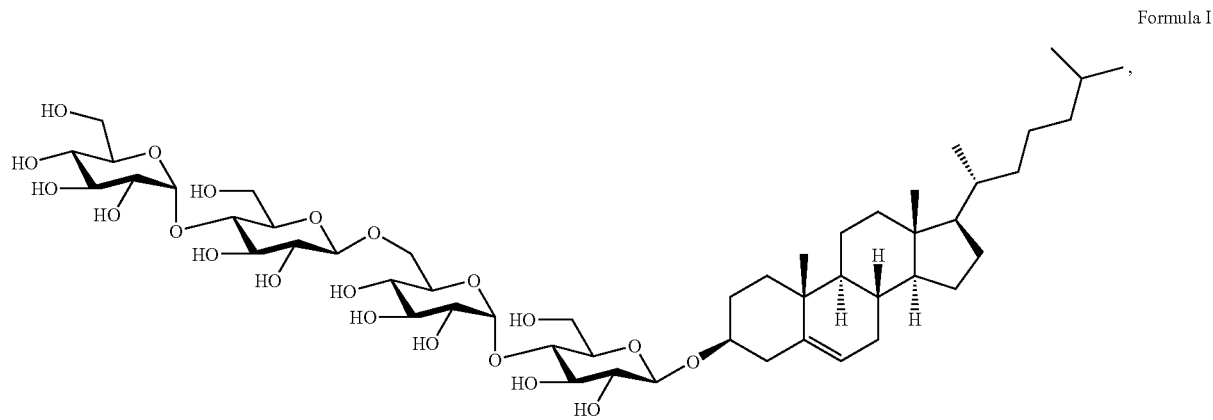

Formula I

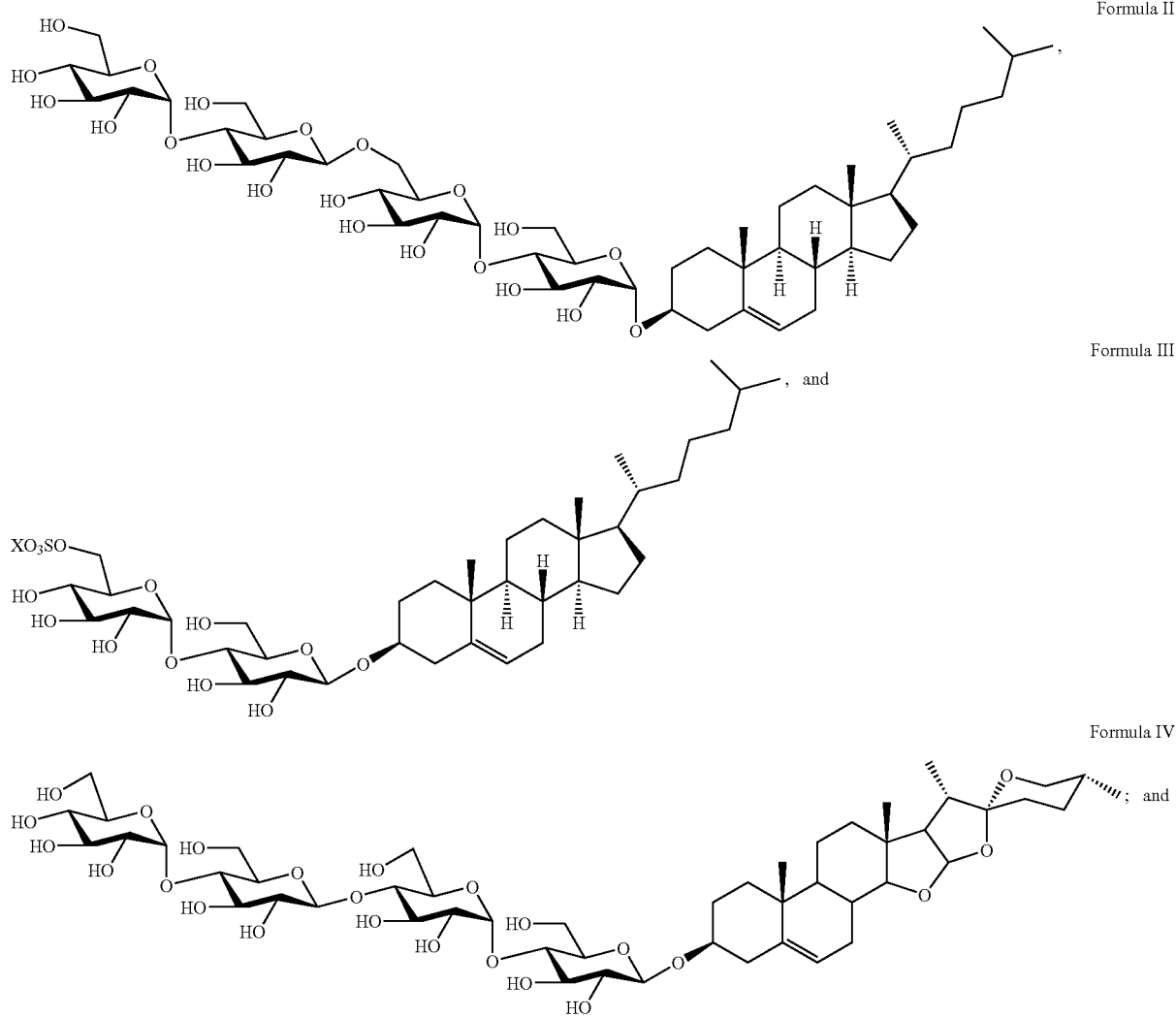
mixing the membrane protein and the at least one cholesterol derivative to reconstitute membrane protein suitable for in vitro biochemical and structural studies.
10. The method according to claim 9, wherein the membrane protein is a G-protein coupled receptor (GPCR).
11. The method according to claim 9, wherein the membrane protein is a transmembrane protein.
* * * * *